United States Patent [19]

Papritz et al.

[11] Patent Number: 5,000,560
[45] Date of Patent: Mar. 19, 1991

[54] APPARATUS FOR EXAMINATION AND TREATING AN EYE

[75] Inventors: Stephan Papritz, Schliern, Switzerland; Eckhard Schröder, Eckental, Fed. Rep. of Germany

[73] Assignee: Haag-Streit AG, Liebefeld, Fed. Rep. of Germany

[21] Appl. No.: 337,423

[22] Filed: Apr. 13, 1989

[30] Foreign Application Priority Data

Apr. 20, 1988 [CH] Switzerland ............... 1455/88

[51] Int. Cl.⁵ ............................................. A61B 3/10
[52] U.S. Cl. ...................................... 351/214; 351/221
[58] Field of Search ............... 351/214, 215, 216, 217, 351/220, 221; 606/4

[56] References Cited

U.S. PATENT DOCUMENTS

| 4,669,837 | 6/1987 | Schirmet et al. | 351/221 |
| 4,854,693 | 8/1989 | Ichihashi et al. | 351/221 |
| 4,865,441 | 9/1989 | Reis | 351/214 |

FOREIGN PATENT DOCUMENTS

| 0030210 | 8/1984 | European Pat. Off. |
| 0225699 | 6/1987 | European Pat. Off. |
| WO87/05495 | 3/1987 | PCT Int'l Appl. |

Primary Examiner—Rodney B. Bovernick
Attorney, Agent, or Firm—Marks Murase & White

[57] ABSTRACT

A coupling mirror (13) for coupling in a laser beam (14) is located in the optical axis of a slit illumination (4,7). A pair of prisms (11) is provided between this coupling mirror 913) and the tube objective (9) of the illumination tube (1), this pair of prisms splitting the light beam of the slit illumination up into two partial beams (12) situated at the side of the coupling mirror (13). As well the slit illumination as the laser beam are focused in a place (16) in the eye by a front objective (15). This design allows the use of a conventional illumination tube which may be rotated together with the slit diaphragm (7) in order to change the direction of the slit image in the eye. For all angular positions of the slit diaphragm a good brightness of the slit illumination is hereby achieved.

16 Claims, 2 Drawing Sheets

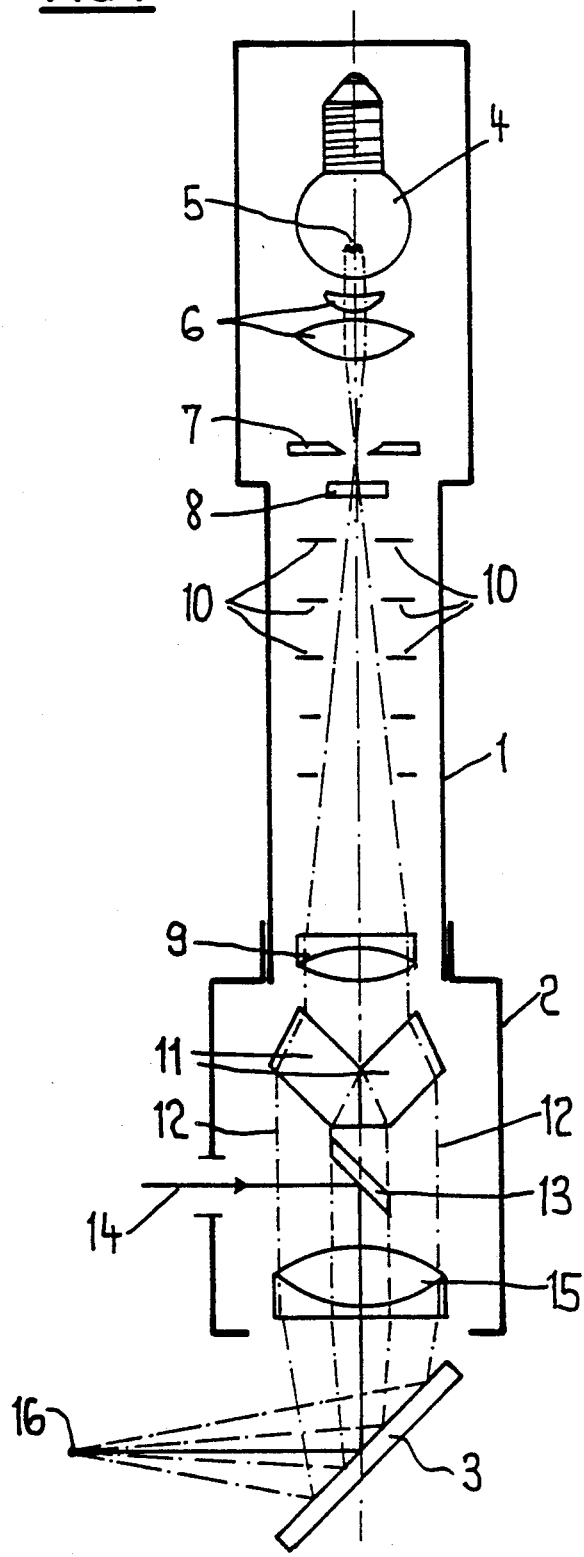
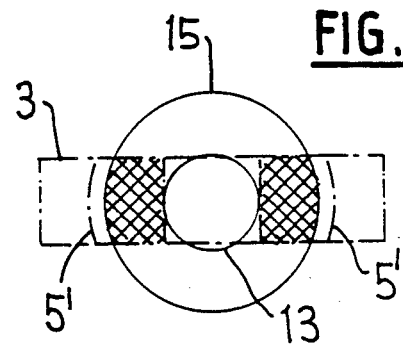
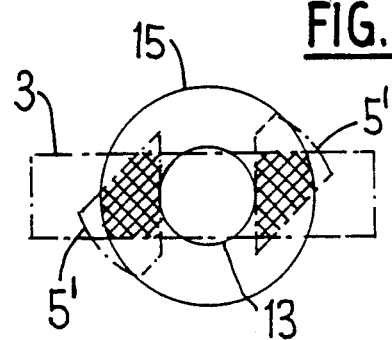
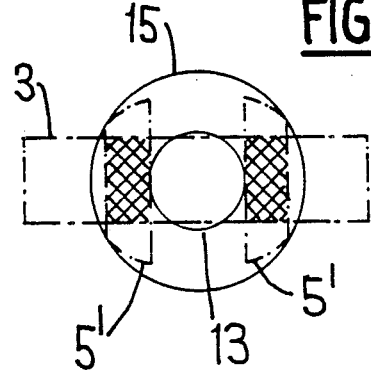

APPARATUS FOR EXAMINATION AND TREATING AN EYE

BACKGROUND OF THE INVENTION

This invention relates to an apparatus for examination and treating an eye, having optical means including an illumination tube for illumination of the eye, a laser beam source and means for optically coupling the laser beam into said optical illuminating means for laser coagulation. Apparatus of this type, particularly slit lamps are well known in the art.

One of the known embodiments has a semi-transparent mirror in its illumination tube, the illumination light passing through this mirror and the entering laser beam being reflected into the axis of the illumination optic by said semi-transparent mirror (DE-A-2611933). While this prior apparatus is simple it involves substantial light losses as well for the illumination as for the laser beam.

In order to avoid at least a part of these drawbacks it has also been known to provide a pair of prisms immediately after the condenser in the illumination tube, these prisms spiting the illumination rays into two lateral partial rays passing at the side of the mirror provided for coupling the laser beam into the illumination optic. The laser beam and both partial beams of illumination rays are reflected into the eye by separate mirrors (EP-A-0225699). However, this embodiment also has various drawbacks. It needs a special design of the illumination tube with additional prisms, and this illumination tube has to have a larger diameter. Therefore, it is not possible to use the illumination tube of an existing diagnostic slit lamp. Rotation of the slit diaphragm and of the whole illumination tube respectively together with the slit diaphragm which is generally usual and desirable now a days is not possible or is only possible to a limited degree because with larger rotation by up to 90° no light would reach the eye over the reflecting mirror.

SUMMARY OF THE INVENTION

The object of this invention is to avoid the drawbacks mentioned above and to achieve additional advantages. According to this invention said means for optically coupling the laser beam into the optical illuminating means comprise a mirror and optical expanding means for expanding the path of the illumination rays, said expanding means being located between said mirror and the objective of said illumination tube. Under these circumstances a conventional illuminating tube without any modification may now be used. It was further found that the slit diaphragm and the whole illuminating tube respectively together with the slit diaphragm may be rotated by up to 90° without losing substantially in brightness of the slit image. It was also found that with a given illuminated surface in the illumination objective a slit image of double brightness is obtained compared with the embodiment according to EP-A-0225699. Therefore, a surprising number of advantages are achieved.

BRIEF DESCRIPTION OF THE DRAWINGS

This invention will now be explained in more detail with reference to an embodiment and some modifications illustrated in the drawings.

FIG. 1 is a schematic illustration of the embodiment,

FIGS. 2 to 4 show the cross sections of the partial beams of rays of a slit illumination in the front objective and FIGS. 5 to 9 show modified embodiments.

DESCRIPTION OF THE PREFERRED EMBODIMENT

Figure 5:
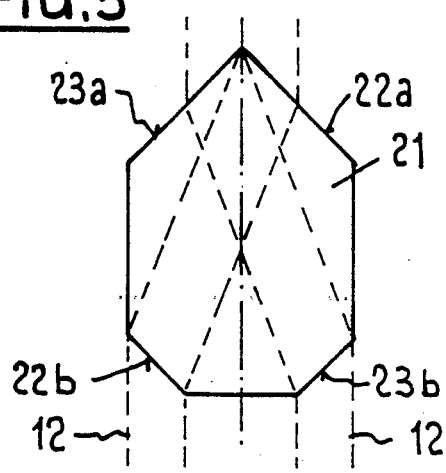

FIG. 1 schematically shows an illumination tube 1 which is mounted for rotation round its vertical axis in a tube 2. An illumination mirror 3 is located below the tube 2. The tube 2 and the illumination mirror 3 are arranged in rigid mutual position on a swinging arm not shown in the drawing of the slit lamp. An incandescent lamp 4 having an incandescent helix 5 is located in the illumination tube 1, whereby the axis of the incandescent helix 5 is in the drawing plane. A condensor 6, a slit diaphragm 7, a filter 8 and a tube objective 9 are disposed below the incandescent lamp. Screens 10 for reducing scattered light in the illumination tube are disposed between the filter 8 and the tube objective 9 which forms an image of the slit diaphragm at infinity. This design of the illumination tube corresponds to the usual design for slit lamps.

A pair of reduction prisms 11 are located in the tube 2 below the tube objective 9. As shown in FIG. 1 this pair of prisms splits the beam of parallel rays leaving the tube objective up into two partial beams of rays 12 displaced outwardly. These beams of rays pass laterally outside a coupling mirror 13 of circular shape in axial protection for reflecting a laser beam 14 entering in radial direction into the tube 2. This laser beam as well as the partial beams of rays 12 pass through a front objective 15 onto the illumination mirror 3 by which they are deflected for forming the slit image and the laser coagulating spot respectively at the place 16.

From FIG. 1 it is seen that the rays of illumination are not obstructed or cut-off by the mirror 13 for coupling the laser beam 14 into the illumination system. Therefore, no mutual discrimination of the illumination system and of the coupling in of the laser beam and particularly no light losses occur in the two systems. In spite of the fact that the illumination mirror 3 should be as narrow as possible in order not to obstruct the path of beams of the stereo microscope of the slit lamp, not shown in the drawing, a sufficiently bright slit image is obtained for all angular positions of the slit diaphragm 7 in a surprising manner. These conditions are schematically illustrated in FIGS. 2 to 4. The relatively narrow illumination mirror 3 is indicated by 3. The opening of the front objective is indicated at 15, the diameter of the coupling mirror 13 and of the laser beam respectively in the front objective is indicated by 13 and the partial images of the incandescent helix 5 are indicated by 5'. From FIG. 2 is thereby seen that with the incandescent helix in parallel position to the longitudinal direction of the mirror 3 (according to FIG. 1) the cross section of the illumination beams of rays indicated by the hatched surfaces has an optimum size.

FIG. 3 shows the conditions with the illumination tube rotated by 45° with the slit diaphragm 7 and the incandescent helix turned accordingly. The partial images of the incandescent helix are displaced outwardly by the prisms 11 but turned by 45°. It is seen that the cross sections of the two illumination beams of rays are of only slightly smaller surface than with optimum yield according to FIG. 2.

FIG. 4 shows the conditions with the illumination tube 1 and the slit diaphragm 7 and incandescent helix 5 rotated by 90°. The partial images 5' of the incandescent helix are now in a position transversal to the longitudinal axis of the mirror 3 and they are displaced outwardly by the prisms 11. In this case the cross sections of the beams of illumination rays still are at least half the cross sections with optimum position according to FIG. 2. Therefore, the slit image still is at least half as bright as with optimum position this being practically hardly recognizable and which is in any case no disadvantage.

FIGS. 5 to 9 show modified embodiments of the optical means for expanding the path of illumination beams. According to FIG. 5 an undivided prism 21 having pairs of parallel surfaces 22a,22b and 23a,23b respectively is provided by which the entering beam of rays is split up in two partial beams 12 crossing each other and leaving the prism in a distance from each other.

Figure 6:
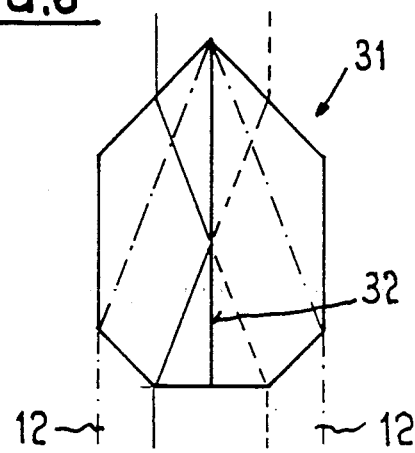

FIG. 6 shows an optic 31 consisting of two separate symmetric prisms the outer form of which corresponds to the same of the prism 21 according to FIG. 5. The joint surfaces 32 of the two prisms have a mirror coating so that the partial beams refracted inwardly at the entry are reflected and do not cross each other but are only reversed in themselves.

Figure 7:
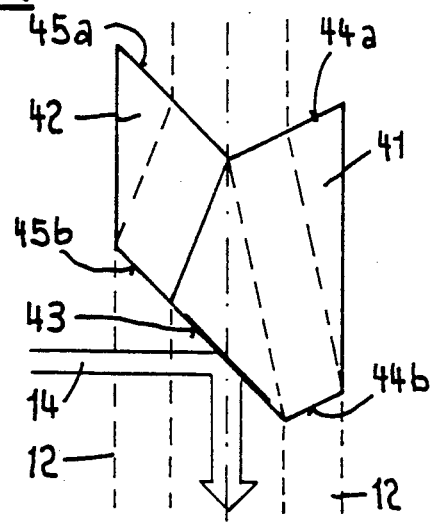
Figure 8:
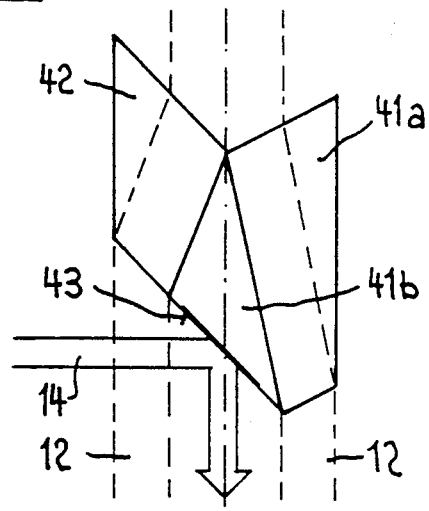
Figure 9:
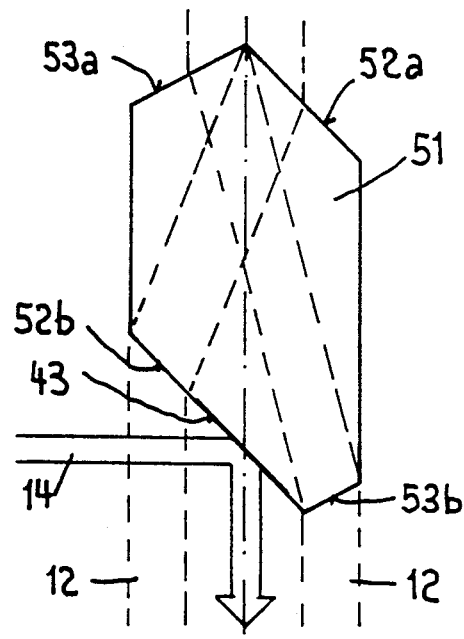

FIGS. 7 to 9 show modified embodiments of the expanding optic in which the prisms for expanding the path of illumination beams are combined with and serve as a carrier for the mirror for coupling in the laser beam.

According to FIG. 7 two prisms 41 and 42 are connected to each other and produce the parallel partial beams 12 substantially according to FIG. 1. The prism 41 has a surface 43 with a mirror coating which serves for reflection of the entering laser beam 14. Due to the inclined surface 43 coated by the mirror the prism 41 has to be longer than the prism 42. The refractive surfaces 44a and 44b at the entry and exit thus have smaller inclination than the refractive surfaces 45a and 45b of prism 42 in order to obtain a symmetrical expansion of the beam of illuminating rays.

FIG. 8 shows an optic similar to the one of FIG. 7 wherein, however, the prism 41 is divided up into two prisms 41a and 41b. The wedge-shaped prism part 41b has no function for expanding the beam of illumination rays but it serves with its surface 43 having a mirror coating for reflecting the laser beam 14.

FIG. 9 shows an undivided prism 41 similar to the one according to FIG. 5 but of a symmetric shape in order to serve for reflection of the laser beam 14 by its surface 43 having with a mirror coating. In this case the pairs of refractive surfaces 52,52b and 53,53b have different inclinations in order to obtain a symmetrical expansion or spreading into partial beams 12 in spite of the different optical length.

In the modified embodiments according to FIGS. 7 to 9 pairs of refractive surfaces of different inclination are provided in order to obtain a symmetrical expansion into two partial beams 12. However, it would be possible to provide pairs of refractive surfaces of the same inclination and thereby to effect an expansion into two partial beams 12 which are asymmetric to the optical axis of tube 1. It would also be possible to displace outwardly only one part of the beam leaving the objective 9 and to let the other part pass without displacement. In this case the mirror surface 43 and the entry of the laser beam 14 should be located in such a way that the reflected laser beam again lies symmetrically between the two partial beams 12. The front objective should also be located symmetrically to the partial beams 12 and to the laser beam 14 that is in an axis displaced relatively to the optical axis of tube 1.

In the embodiments according to FIGS. 1, 5 and 6 the prisms might be rotatable by 90° in order to selectively cooperate with a mirror 3 of which the greater dimension is parallel to or transversal to the plane of the drawing. In many cases the whole slit illumination may be tilted round an axis perpendicular to the plane of drawing in FIG. 1 relatively to the mirror 3, and in this case a T-shaped mirror 3 might be used which is narrow in its upper part and larger in its lower part. According to the inclination of the slit illumination the prisms might then be adjusted accordingly in order to expand the beam in the plane of the drawing (FIG. 1) or transversally to the same.

We claim:

1. An apparatus for examination and treating an eye, having optical means including an illumination tube for illumination of the eye, a laser beam source and means for optically coupling the laser beam into said optical illuminating means for laser coagulation, said means for optically coupling the laser beam into the optical illuminating means comprising a mirror and optical expanding means for expanding the path of the illumination rays, said expanding means being located between said mirror and the objective of said illumination tube.

2. An apparatus according to claim 1, wherein said illuminating means comprise a slit diaphragm for projecting a slit image into the eye.

3. An apparatus according to claim 1, wherein the optical expanding means comprise a pair of prisms.

4. An apparatus according to claim 3, wherein said prisms have an opposite inclination relative to the optical axis, each of said prisms having two plane-parallel optically active surfaces.

5. An apparatus according to claim 1, wherein the optical expanding means are rotatable around the axis of the illuminating means.

6. An apparatus according to claim 1, wherein said optical expanding means comprise a reflecting surface for coupling said laser beam into said illuminating means.

7. An apparatus according to claim 6, wherein said optical expanding means comprise asymmetrically formed or disposed prisms having parallel pairs of refractive surfaces of different inclination for obtaining a symmetrical expansion of the path of illumination rays.

8. An apparatus according to claim 6, wherein said optical expanding means comprise asymmetrically formed or disposed prisms having pairs of refractive surfaces of equal inclination for obtaining an asymmetrical expansion of the path of illumination rays.

9. An apparatus for examining and treating an eye, comprising:

optical illuminating means including an illumination tube for illuminating the eye with illumination rays, a laser beam source and means for optically coupling the laser beam into said optical illuminating means for laser coagulation;

wherein said means for optically coupling the laser beam into the optical illuminating means comprising a mirror and optical expanding means for expanding the path of the illumination rays;

wherein said illumination tube comprises a light source, a slit diaphragm and a tube objective, and is rotatable relative to a front objective which is common to the illumination rays and the laser beam; and wherein said expanding means is located between said mirror and said tube objective.

10. An apparatus according to claim 9, wherein said illuminating means comprises a slit diaphragm capable of projecting a slit image into the eye.

11. An apparatus according to claim 9, wherein said optical expanding means comprises a pair of prisms.

12. An apparatus according to claim 9, wherein said prisms have an opposite inclination relative to the optical axis, and each of said prisms have two plane-parallel optically active surfaces.

13. An apparatus according to claim 9, wherein said optical expanding means is rotatable around the axis of the illuminating means.

14. An apparatus according to claim 9, wherein said optical expanding means comprises a reflecting surface for coupling said laser beam into said illuminating means.

15. An apparatus according to claim 14, wherein said optical expanding means comprises asymmetrically formed or disposed prisms having parallel pairs of refractive surfaces of different inclination for obtaining a symmetrical expansion of the path of illumination rays.

16. An apparatus according to claim 14, wherein said optical expanding means comprises asymmetrically formed or disposed prisms having pairs of refractive surfaces of equal inclination for obtaining an asymmetrical expansion of the path of illumination rays.

* * * * *

UNITED STATES PATENT AND TRADEMARK OFFICE
CERTIFICATE OF CORRECTION

PATENT NO. : 5,000,560
DATED : March 19, 1991
INVENTOR(S) : PAPRITZ ET AL.

It is certified that error appears in the above—identified patent and that said Letters Patent is hereby corrected as shown below:

On title page,
Item [73], "Haag-Streit AG, Liebefeld, Fed. Rep. of Germany" should be -- Haag-Streit AG, Liebefeld, Switzerland --.

Signed and Sealed this

First Day of March, 1994

Attest:

BRUCE LEHMAN

Attesting Officer     Commissioner of Patents and Trademarks